US005623056A

United States Patent [19]

Tykocinski et al.

[11] Patent Number: 5,623,056

[45] Date of Patent: Apr. 22, 1997

[54] CDS DERIVATIVES AND METHODS OF USE FOR CELLULAR MODULATION AND ENHANCEMENT OF CELLULAR ENGRAFTMENT

[75] Inventors: Mark L. Tykocinski, Shaker Heights; David R. Kaplan, Cleveland Heights, both of Ohio

[73] Assignee: TKB Associates Limited Partnership, Pepper Pike, Ohio

[21] Appl. No.: 174,583

[22] Filed: Dec. 28, 1993

Related U.S. Application Data

[63] Continuation of Ser. No. 429,401, Oct. 31, 1989, which is a continuation-in-part of Ser. No. 323,770, Mar. 15, 1989, abandoned.

[51] Int. Cl.[6] ........................ C07K 14/705; C07K 14/725

[52] U.S. Cl. ........................ 530/403; 530/395; 530/402; 530/868; 424/193.1; 424/194.1

[58] Field of Search .................................. 424/88, 184.1, 424/193.1, 194.1; 514/2, 8, 12; 530/395, 402, 403, 350, 868

[56] References Cited

FOREIGN PATENT DOCUMENTS 0347143 12/1989 European Pat. Off. .
9013629 11/1990 WIPO .

OTHER PUBLICATIONS

AIDS/HIV Experimental Treatment Directory, (Abrams, et al, ed.) vol. 2(2), pp. 100–101, rec. Sol CD.
B.E. Bierer, et al. Ann. Review. Immunol. 1989 vol. 7:579–99 The Biological Roles of . . . .
Y. Rosenstein, et al. J. Exp. Med. 169: 149–160 Jan. 1989 Direct Evidence for Binding of CD8 . . . .
P.J. Fink, Ann. Rev. Immunol. 6: 115–137, 1988 "Veto Cells.".
M.L. Tykocinski, et al., PNAS 85: 3555–9, "Glycolipid reanchoring of T–lymphocyte . . . ".
M.A.J. Ferguson, Ann. Rev. Biochem. 57:285–320. "Cell Surface Anchoring of Proteins . . . ".
J.E. Hambour, et al. J. Exp. Med. Oct. 1988. vol. 168: 1237–45. "Functional Consequences of antisense . . . ".
D.R. Kaplan, et al. PNAS 86:8512–15 Nov. 1989 "An Immunoregulatory function for the CD8 molecule."
D.R. Littman, Ann. Rev. Immunology 5:561–84 1987. "The Structure of the CD4 and CD8 genes."
N. Fasel, et al. PNAS 86:6858–62. Sep. 1989 "In vitro attachment of glycosylinositolphospholipid . . . ".
D.R. Littman, et al. Cell 40:237–246 Feb. 1985 "The Isolation and Sequence of the Gene Encoding T8 . . . ".
Kaplan et al., Proc. Natl. Acad. Sci. USA, 86:8512–15, 1988.
Rammensee, Intern. Rev. Immunol. 4:1754–191, 1989.
Claesson, Cellular Immunology 109:360–370, 1987.
Melchers et al., Scand. J. Immunol. 30:99–109, 1989.
Green et al., Ann. Rev. Immunol 1:43963, 1983.
Fink et al., J. Exp. Med. 157:141–154, 1983.
Kung et al., PCT WO 87/05912, Oct. 8, 1987, (T–Cell Sciences).
Vremec et al., J. Exp. Med. 176, pp. 47–58, 1992.
Zoller, M. J., et al., Methods in Enzymology 154:329–350 (1987), "Oligonucleotide–directed mutagenesis: a simple method using two oligonucleotide primers and a single stranded DNA template".
Fink, P. J., et al., J. Immunology 133(4):1775–81 (1984), "Cloned cytotoxic ells can suppress primary cytotoxic responses directed against them".
Lanzavecchia, A., Nature 319:778–783 (Feb., 1986), "Is the T–cell receptor involved in T–cell killing?".
Paul, W. F. (ed.), *Fundamental Immunology*, 3rd edition (1993), pp. 700–702 & 726 from Chapter 18 "Immunological Tolerance".
Sambhara, S. R., et al., Science 252:1424–1427 (7 Jun. 1991), "Programmed cell death of T cells signaled by the T cell receptor and the alpha–3 domain of Class I MHC".
Zhang, L., et al., J. Immunology 148:3740–3745 (Jun. 15, 1992), "Peripheral deletion of mature $CD8^+$ antigen–specific T cells after in vivo exposure to male antigen".
Bowie, J. U., et al. Science 247:1306–1310 (16 Mar. 1990).
Briand, J. P., et al., J. Immunol. Meth. 78:59–69 (1985).
G.D. Fasman in *Proteins:Form and Function*, pp. 135–145 (1990), Elsevier Trends Journals.
Alber T., Annu. Rev. Biochem. 58:765–98 (1989). "Mutational effects on protein stability".

*Primary Examiner*—Thomas M. Cunningham
*Attorney, Agent, or Firm*—Lyon & Lyon

[57] ABSTRACT

Specific and nonspecific immunomodulation, enhancement of cellular engraftment, and modulation of nonimmune cells are achieved by using various membrane-binding and soluble CD8 compositions.

25 Claims, No Drawings

CDS DERIVATIVES AND METHODS OF USE FOR CELLULAR MODULATION AND ENHANCEMENT OF CELLULAR ENGRAFTMENT

This application is a continuation of application Ser. No. 07/429,401, filed Oct. 31, 1989, which is a continuation-in-part of application U.S. Ser. No. 07/323,770 filed Mar. 15, 1989 abandoned.

FIELD OF THE INVENTION

The present invention relates to immunosuppression and immunotolerization for the treatment of subjects in need of the abrogation of untoward immunological reactivities and of subjects in need of the enhancement of cell, tissue and organ transplant survival. More particularly, it relates to the use of CD8 (hereinafter defined) and its derivatives as immunomodulators to effect said therapeutic objectives. The present invention also relates to broader therapeutic uses for CD8's inhibitory ligand activity in the modulation of cells outside of the immune system.

BACKGROUND

In that application, included herein in its entirety by reference, antigen-specific (hereinafter referred to as "specific") immunosuppression and immunotolerization in subjects in need of the selective suppression of immune responses to defined antigens is achieved through the pharmaceutical use of CD8, and derivatives thereof. This therapeutic strategy is predicated upon our discovery that the CD8 molecule inhibits immune and other cells that are being costimulated with certain secondary molecules (hereinafter referred to as "ligands"; vide infra). Although a variety of immunosuppressive capabilities have been previously ascribed to T lymphocytes with a CD8-positive phenotype, the role of the CD8 molecule itself as a critical molecular determinant of inhibitory activity exerted by these cells was unknown until said disclosure. Moreover, prior to said disclosure of CD8's inhibitory ligand function, the only known function for CD8 was its molecular accessory function, wherein it plays an obligatory role in T cell activation through the T cell receptor complex.

At the present time, specific immunotolerization therapies, primarily centered around the administration of specific antigen in association with additional substances, are relatively ineffective. Therapies for transplant, allergic and other subjects n need of immunosuppression most commonly employ generalized, nonspecific immunosuppressive agents. These therapeutic agents, which include X-irradiation, cytotoxic drugs, cyclosporin A, corticosteroids, and antilymphocytic serum, suffer from significant side effects involving multiple immune and nonimmune organs. Furthermore, in the case of clinical transplantation, no effective strategies for biochemically altering grafts in vitro to prolong their survival in a host have been described.

An object of the present invention is to provide an effective process for specific immunosuppression and immunotolerance induction, which process comprises the use of CD8 compositions.

Another object of the present invention is to provide a process, using CD8 compositions, for generalized, nonspecific immunosuppression, which process suffers from fewer side effects than currently available processes, and permits more specific targeting of organs of the immune system than current therapies.

Yet another object of the present invention is to provide a process for biochemically altering grafts prior to transplantation, in a way which enables them to evade immunological rejection mechanisms, and thereby promote their engraftment, which process comprises the use of CD8 compositions.

Still another object of the present invention is to provide a process for prevention of graft versus host disease following bone marrow transplantation, which process comprises the use of CD8 compositions.

Still another object of the present invention is to provide a process for selective modulation of nonimmune cells, which process comprises the use of CD8 compositions.

Other objectives, features and advantages of the invention will be found throughout the following description and claims.

SUMMARY OF THE INVENTION

According to the present invention, there are provided compositions comprising membrane-binding and soluble CD8 peptides, including those genetically engineered, and methods of use for immunomodulation and modulation of nonimmune cells in vivo and in vitro. A pharmacologically active CD8 composition comprises a CD8 peptide associated with one or more secondary ligands that serve to direct CD8's inhibitory ligand activity to specific target cells. This association between CD8 and secondary ligands can be noncovalent and ensue simply from their presence on a common biomembrane (of a cell, liposome, planar membrane, pseudocyte, etc.), or covalent, through linkage in a CD8:ligand conjugate as part of a linear or branched polypeptide chimera. A broad array of CD8:ligand combinations can be used, each of which permits the targeting of CD8's modulatory activity to a specific subset of cells. A preferred embodiment of the present invention, particularly applicable for the purpose of specific T cell immunosuppression and immunotolerization, comprises a CD8 composition in which CD8, or a functional CD8 domain, is associated with a peptide derivative of a major histocompatibility complex (MHC) protein. A defined nominal antigen peptide (NAP) can be secondarily associated with the MHC component of said composition to permit the induction of specific immunosuppression and immunotolerance for the parental protein encompassing said NAP sequence. Another preferred embodiment of the present invention, particularly applicable for the purpose of mast cell and basophil suppression in the treatment of immunoglobulin E (IgE)-related allergic disorders, comprises a soluble CD8:Fcϵ conjugate wherein CD8, or a functional CD8 domain, is associated with an IgE Fc domain. Yet another preferred embodiment of the present invention, particularly applicable for the purpose of generalized, nonspecific immunosuppression, comprises a soluble CD8:Fc conjugate, wherein CD8, or a functional CD8 domain, is covalently linked to an immunoglobulin (non-IgE) Fc domain. This CD8:Fc conjugate can be used to coat Fc receptor (FcR)-bearing antigen presenting cells, and these cells, in turn, can be used to inhibit immune cells in a nonspecific fashion. Still another preferred embodiment of the present invention, particularly applicable for the purpose of prolongation of graft survival in a transplant recipient, comprises a process wherein a membrane-binding CD8 peptide is used to coat graft cells prior to transplantation, to promote engraftment in a transplant recipient. Still another preferred embodiment of the present invention, particularly applicable for the purpose of prevention of graft versus host disease following bone marrow transplantation, comprises a process wherein a therapeutic biomembrane preparation comprising a CD8 peptide and a MHC peptide corresponding to the transplant recipient's haplotype, or a CD8:MHC conjugate, is used to treat bone marrow cells in vitro prior to transplantation, to inhibit alloreactive immune cells in the donor cell population.

THE PREFERRED EMBODIMENTS

The present invention is directed to methods for cellular modulation, with a focus on cells of the immune system. The compositions and methods for specific immunosuppression, specific immunotolerization and generalized, nonspecific immunosuppression are applicable to, but not restricted to, the clinical settings of transplantation and autoimmune, hypersensitivity, allergic and other immunological disorders.

The present invention is predicated upon our discovery, as disclosed by us in U.S. Set. No. 07/323,770, that the CD8 molecule can function as an inhibitory ligand. The inventors of the present invention previously developed a methodology for stable gene transfer into nontransformed, cloned human T cells (Proc. Natl. Acad. Sci. U.S.A. 85:4010–4014, 1988). This methodology, in turn, enabled the first linking of antisense mutagenesis and T cell cloning technologies. When applied to CD8, in earlier studies, to create T cell clonal phenocopies of null mutations for CD8, this transfection technology permitted a definitive demonstration of CD8's function as an obligatory accessory molecule for the specific activation and killing mediated by CD8-positive cytotoxic T cells (J. Exp. Med. 168:1237–1245, 1988). Another byproduct of our transfection technology, and specifically of our ability to produce CD8-negative antisense mutants, is the insight into CD8's previously unsuspected role in the suppression mediated by CD8-positive T cells, as disclosed in the present invention.

Specifically, we have established that a native or genetically engineered CD8 peptide can inhibit T cells and other cells when said CD8 peptide is associated with a second ligand that would otherwise function as a cellular activator. For instance, in the case of T cells, the second ligand can be an allo-MHC molecule or a specific (processed) antigen associated with a self-MHC molecule. CD8's immunomodulatory activity has been assessed experimentally by our group using several types of in vitro cellular proliferation and cytotoxicity assays, employing a variety of sense and antisense CD8 transfectants and controls. Cells for these studies were obtained from subjects JH (HLA haplotype:A2, 3; B7,44;DR2,4), DK (HLA haplotype A2,24;B13,50;DR2, 7), and MW (HLA haplotype A1,31;B8;DR3). Our findings include the following:

(i) The proliferative response of responding cells to irradiated, allogeneic stimulator cells in mixed cell cultures is dependent upon the absence of CD8 on the irradiated stimulators. In one such experiment, $10^5$ responder peripheral blood mononuclear cells (PBMC) from DK were combined with stimulators comprising either $2\times10^4$ irradiated (5000 R), syngeneic cells of the cloned, CD8-positive T cell line JH.ARL.1 (derived from JH and with known allospecificity for HLA-B35) or $2\times10^4$ irradiated (5000 R), CD8-negative antisense CD8 transfectant derivatives of the JH.ARL.1 line, in quadruplicate wells of a 96-well flat-bottom microtiter plate in RPMI 1640 medium with 10% fetal bovine sera. Cells were cocultured for 4–7 days at 37° C., adding 1 μCi of [$^3$H]-thymidine to each well during the last 18 h. The cells were harvested, and the radioactivity incorporated was counted. A proliferative response was observed for the CD8-negative, but not for the CD8-positive, stimulator at all time-points. This was confirmed using a sense, instead of an antisense, transfection approach. In one such experiment, $10^5$ responder PBMC from MW were combined with stimulators comprising either $2\times10^4$ irradiated (15,000 R), nontransfected K562 human eyrthroleukemia cells or K562 cells transfected with an irrelevant expression construct, both of which are CD8-negative, or $2\times10^4$ irradiated (15,000 R) sense CD8 K562 transfectants (CD8-positive) in the proliferation assay as described. Again, only the CD8-negative, but not CD8-positive, cells were able to stimulate proliferation.

(ii) The proliferative response of responding cells to irradiated, allogeneic stimulator cells and their capacity for cytotoxicity against allogeneic target cells can be inhibited by the simultaneous addition of third party cells, if the latter cells bear both CD8 and a specific alloantigen that is recognized by the responding cells, and thus such cells function in an immunosuppressive "veto-like" capacity. In one such experiment, $10^5$ responder PBMC from DK were combined with $5\times10^4$ irradiated (5000 R) stimulator PBMC from JH and varying numbers of cloned T cells as putative inhibitors, originating from JH, comprising either CD8-positive or CD8-negative (antisense) JH.ARL.1 transfectants. Inhibition of the proliferative response was observed only for the CD8-positive third party cells, and the potency of the inhibition was demonstrated by the finding of 33% and 78% inhibition at inhibitor-:stimulator cell ratios of 1:500 and 1:5, respectively. Absence of inhibition upon combining JH responders, DK stimulators, and JH cloned (CD8-positive) T cell inhibitors established that a specific recognition event is required between responders and CD8-positive inhibitors in order for inhibition to occur. We further demonstrated CD8-dependent inhibition of cytotoxic T cell generation in MLR cultures. Allogeneic cultures were set up in 24-well plates in a volume of 2 ml of RPMI 1640 containing fetal bovine sera. $10^6$ responder PBMC from MW, $5\times10^5$ irradiated (5000 R) stimulator PBMC from JH, and $10^5$ irradiated (CD8-positive or CD8-negative antisense phenocopies) cloned JH.ARL.1 cells were added per well. After incubation for 6 days at 37° C., cells were harvested, and dead cells removed by histopaque density gradient centrifugation. A [$^{51}$Cr]-release assay (Cell. Immunol. 88:193–206, 1984) was performed with EBV-transformed JH (LCL) B lymphocytes as targets. Inhibition was evident only with CD8-positive third party cells, and maximal inhibition was achieved when these cells were added at the initiation of the cultures or by day 2. These findings with JH.ARL.1 lymphoid cells as inhibitors were confirmed with non-lymphoid K562 cells as stimulators and inhibitors. In one such experiment, $10^5$ responder PBMC from JH, $5\times10^4$ irradiated (20,000 R) K562 stimulators, and putative inhibitors, comprising either irradiated CD8-negative K562 cells or CD8-positive sense K562 transfectants were used. Marked CD8-dependent inhibition was observed with as few as $5\times10^2$ inhibitors. In another experiment, irradiated (15, 000 R) immortalized human bone marrow stromal cells were used in place of K562 cells, with analogous results.

(iii) The proliferative response of responding cells to irradiated, allogeneic stimulator cells can be blocked by pretreatment of the responding cells with irradiated, or otherwise metabolically inactivated, third party "tolerogenic" cells, if the latter cells bear both CD8 and a specific alloantigen that is recognized by the responding cells. In one such experiment, $10^5$ PBMC responders from JH were incubated with fixed (air-dried, with or without post-treatment with 2% paraformaldehyde in phosphate-buffered saline for 2 h at 37° C.) CD8-positive or CD8-negative K562 or human bone marrow stromal cell transfectants for 48 h in RPMI 1640 supplemented with 10% fetal bovine sera, in quadruplicate 96-well plates. PBMC so pre-treated were recovered, stimulated with CD8-negative counterparts for 18 h in the presence of 0.5 μCi/well [$^3$H ]-thymidine, and [$^3$H ]-thymidine incorporation was measured. The data indicated a marked and specific CD8-dependent tolerization amidst the responders.

Hence, the inhibition directed by CD8 can be used to both immunosuppress and immunotolerize. Moreover, assays similar to the ones described have indicated that CD8-mediated inhibition is applicable for the immumomodulation of responses to specific antigens other than alloantigens, as well as for the modulation of nonimmune cells (vide infra).

Further experiments have elucidated the functional requirements for the CD8 ligand itself. Two forms of CD8 are known to be present on human T lymphocyte surfaces: an α:α homodimer and an α:β heterodimer. CD8α (herein referred to as "CD8") can function as an inhibitory ligand as a monomer, and hence the CD8β chain is not required for inhibition. CD8β requires CD8α in order to be efficiently expressed on the cell surface in native cellular settings. The CD8 peptide need not be expressed on immune cells per se, and hence T cell-specific factors are not required for CD8-mediated inhibition. Furthermore, glycoinositolphospholipid-modified CD8, when anchored to membranes, and even CD8 anchored to fixed cells, both maintain the inhibitory capacity of the native CD8 molecule. Hence, CD8-mediated inhibition is dependent upon the physiological status of the responding (target) cell, but is independent of the physiological status of the inhibitory cell. The latter point lays the groundwork for developing compositions comprised of membrane-binding CD8 derivatives linked to liposomes or other membranous therapeutic vehicles or of soluble CD8 derivatives.

One embodiment of a CD8 composition according to the present invention comprises the complete extracellular region of CD8 [encompassing amino acids 1 (Ser) through 160 (Cys) of processed human CD8; for CD8 coding sequence, see Littman, D. R., et al., Cell 40:237–246, 1985]. An alternative CD8 composition is comprised of a functional domain within the extracellular region of CD8, such as one corresponding to the immunoglobulin V homologue region of CD8 [encompassing amino acids 1 (Set) through 114 (Ala) of processed human CD8]. Protein engineering strategies using recombinant DNA tools for molecularly dissecting a protein such as CD8, to define functionally active subcomponents, are well known to those familiar with the art, and hence can be used to define additional functional CD8 peptide derivatives.

Another embodiment of a CD8 peptide composition according to the present invention comprises a CD8:ligand conjugate, wherein CD8, or a functional peptide derivative thereof, is covalently linked to one or more secondary ligand molecules, the latter permitting the selective targeting of, and providing a costimulatory signal to, a specific subset of cells. The second ligand molecule of such a "bipartite CD8 ligand" can be peptidic or nonpeptidic in nature. In the case of peptide ligands, the CD8 and second ligand peptides can be linked in a linear or branched polypeptide chimera (vide infra). Additional ligands (third, etc.) can be similarly linked, and by utilizing such a "multipartite CD8 ligand," the effectiveness of the invention can be enhanced. Furthermore, membrane-binding or soluble forms can be produced. Several examples of CD8:ligand conjugates will now be cited, which serve to illustrate, but in no way restrict, the types of such CD8-based conjugates that can be produced and used for cellular modulation.

One example of a CD8:ligand conjugate is a CD8:MHC conjugate, wherein a CD8 peptide is covalently linked to a class I or class II MHC protein, or a functional peptide derivative thereof. Functional MHC peptide derivatives are comprised of those domains that are sufficient, and maintain the capacity in the synthetic peptide, for constituting a nominal antigen peptide (NAP) binding site. In the case of class I MHC, which is composed of a polymorphic, transmembrane heavy chain and a noncovalently-associated, nonpolymorphic, non-membrane-anchored $\beta_2$-microglobulin light chain, the $\alpha_1$ and $\alpha_2$ extracellular domains of the heavy chain together constitute a NAP binding site (Bjorkman, P. J., et al. Nature 329:506–512, 1987). In the case of class II MHC, which is composed of noncovalently-associated, polymorphic, transmembrane α and β chains, the $\alpha_1$ domain of the chain and the $\beta_1$ domain of the β chain are sufficient for constituting a NAP binding site (Brown, J. H., et al. Nature 332:845–850, 1988). NAPs can be associated, noncovalently or covalently, with the CD8:MHC conjugate to confer antigenic specificity to said conjugate, and permits targeting of specific T cells.

A second example of a CD8:ligand conjugate is a CD8:unprocessed antigen conjugate, wherein a CD8 peptide is covalently linked to an unprocessed antigen, the latter constituting a ligand for immunoglobulins on the surface of specific B cells. Examples of unprocessed antigens include allergens, such as benzyl-penicilloyl, insulin, ovalbumin, lactalbumin, grass pollens, ragweed pollen, ragweed antigen E, tree pollens, bee venom, snake venom, and house dust mite, and self-antigens. Such conjugates permit targeting of specific B cells and are used to induce antigenic unresponsiveness and tolerance in humoral immune responses.

A third example of a CD8:ligand conjugate is a CD8:Fc conjugate, wherein a CD8 peptide is covalently linked to the Fc domain of an immunoglobulin molecule, or a functional, Fc receptor (FcR)-binding derivative thereof. Fc domains corresponding to any of the immunoglobulin isotypes can be employed for this purpose. Such a conjugate permits targeting of specific classes of Fc-receptor bearing cells. This, in turn, can serve one of two purposes from a functional standpoint. For certain FcR-binding cells, an inhibitory signal will be transduced by the CD8:Fc conjugate. Even in the absence of an inhibitory effect, the CD8:Fc conjugate will bind to the surface receptors, serving to coat the cell surface with CD8. This, in turn, serves to convert an FcR-positive antigen presenting cell into an inhibitory cell.

A fourth example of a CD8:ligand conjugate is a CD8:Fv conjugate, wherein a CD8 peptide is covalently linked to the Fv (antigen-binding) domain of an immunoglobulin molecule, or an Fv-containing peptide. The Fv component confers specificity for specific cell surface-associated molecules bound by the Fv component, and thereby permits targeting of specific cells.

A fifth example of a CD8:ligand conjugate is a CD8:cytokine conjugate, wherein a CD8 peptide is covalently linked to a peptidic cytokine. A broad array of cytokines can be used for this purpose, including colony stimulating factors, interleukins and hormones. Such conjugates permit targeting of specific cytokine receptor-bearing cells.

A sixth example of a CD8:ligand conjugate is a CD8:lectin conjugate, wherein a CD8 peptide is covalently linked to a lectin. A broad array of lectins can be used for this purpose, including conconavalin A and phytohemagglutinin. Such conjugates permit targeting of specific normal and transformed cells bearing defined, lectin-reactive carbohydrate specificities on their surfaces.

A seventh example of a CD8:ligand conjugate is a CD8:anti-Id conjugate, wherein a CD8 peptide is covalently linked to an anti-idiotypic (anti-Id) mimic of a second ligand, such as one of those described heretofore. Additionally, an anti-Id can be used as a mimic of CD8 itself in any of the CD8 compositions described heretofore.

CD8 peptides, comprising either CD8 sequences only or CD8 sequences coupled to peptide or nonpeptidic ligands in CD8:ligand conjugates, can be soluble or membrane-binding. Coding sequences can be genetically engineered to create soluble forms by introducing a translational stop codon into the coding sequences of CD8 and peptide ligands, upstream of the hydrophobic transmembrane domains, using site-specific mutagenesis technologies. Coding sequences can be genetically engineered to create membrane-binding forms by linking, or retaining the linkage of, the coding sequences of CD8 and secondary peptide ligands to: 1) coding sequences for hydrophobic extension peptides of transmembrane proteins; or 2) coding sequences that direct glycoinositolphospholipid modification of peptides inside cells. A glycoinositolphospholipid-modified CD8 peptide represents a preferred embodiment of a membrane-binding CD8 peptide, according to the present invention, since it can be readily incorporated into biomembranes when exogenously added to them.

Linear polypeptide chimeras, in the forms of glycoinositolphospholipid-modified protein intermediates and CD8:ligand conjugates, as disclosed in the present invention, can be readily produced by recombinant DNA technology. Chimeric transcriptional cassettes can be assembled using restriction endonuclease site overlap or the polymerase chain reaction (PCR)-based splice-by-overlap-extension (Horton, R., et al., Gene 77:61–68, 1989) methodologies. To produce glycoinositolphospholipid-modified peptides, the coding sequence for the peptide of interest is linked in-frame to the coding sequence for the 3' end of a protein that naturally undergoes glycoinositolphospholipid modification, such as decay accelerating factor (DAF). The chimeric protein produced in this way undergoes glycoinositolphospholipid modification inside the cell. This glycoinositolphospholipid-modification process was discovered by one of the inventors of the present invention (M. L. T.), and it was first applied to CD8.

(Tykocinski, M., et al., Proc. Natl. Acad. Sci. U.S.A. 85:3555–3559, 1988). To produce CD8:ligand conjugates, the coding sequences for a CD8 peptide, a suitable linker peptide, and the ligand peptide are tandemly linked in-frame. Choice of promoters, for the chimeric gene transcriptional cassette, vectors and host cells will dictate the nature of post-translational modifications introduced into the chimeric protein and the quantity of protein produced. For instance, baculovirus promoters and vectors can be used in insect host cells to produce large quantities of glycosylated CD8 compositions.

We have produced various genetic constructions for generating glycoinositolphospholipid-modified and soluble CD8 peptides. As starting material for these genetic constructions, we either PCR-cloned specific mRNAs from reverse transcribed poly(A+)RNA or obtained cDNA clones for human CD8 (for nucleotide sequence, see Cell 40:237–246, 1985; ATCC deposit no. 59565), human DAF (for nucleotide sequence, see Proc. Natl. Acad. Sci. USA 84:2007–2011, 1987), human class I MHC α heavy chain of the A2 haplotype (for nucleotide sequence, see J. Immunol. 134:2727–2733, 1985), human GM-CSF (Science 228:810, 1985; Proc. Natl. Acad. Sci. USA 82:4360, 1985; ATCC deposit nos. 39754, 57595 and 59171), human IgG1 heavy chain γ1 (for nucleotide sequence, see Nucleic Acids Res. 10:4071–4079, 1982), and human IgE heavy chain ε (for nucleotide sequence, see Cell 29:691–699, 1982). Examples of CD8 peptides include, but are not restricted to, the following:

(i) Production of a glycoinositolphospholipid-modified CD8 peptide, encompassing the complete extracellular domain of CD8 (through asp 161), by a restriction endonuclease-based methodology. Specifically, the 3' end of DAF cDNA is cut at the Ava II site (nucleotide position 858), this site is blunted by filling-in with Klenow fragment, and the CD8 coding segment cut at the EcoRV site (nucleotide position 609) is blunt-end ligated to the filled-in Ava II site of DAF. This creates a CD8:DAF chimera, which undergoes glycoinositolphospholipid-modification inside cells (Tykocinski, M. L., et al. Proc. Natl. Acad. Sci. USA85:3555–3559, 1988).

(ii) Production of a glycoinositolphospholipid-modified CD8 peptide, encompassing the immunoglobulin V-homologue domain of CD8 (through ala 114), by a splice-by-overlap extension methodology. Specifically, the CD8 sequence (spanning nucleotide positions 31 through 470) is PCR-amplified (denaturing 94° C., 2'; annealing 50° C., 2'; polymerizing 72° C., 2'; using Perkin Elmers-Cetus, Inc. thermal cycler and Gene-Amp kit) with the oligonucleotide primers a [5'-GGATCCAAGCTTCTCGAGAGCTTCCGC-CAAGCAGC-3'] and b[5'-GAACTGTTGGTGGGACCGCTGGCAGGAAG-3'], and the DAF sequence (spanning nucleotide positions 859 through 2008; starting at val 258) is PCR-amplified with the oligonucleotide primers c [5'-CAGCGGTC-CCACCAACAGTTCAGAAACCT- 3'] and d[5'-GAGCTCGAGAAGCTTTGGGATCATTTATTT-3']. Primer a adds BamHI, Hind III, and XhoI sites to the 5'-end, and primer b adds Hind III, XhoI, and Sac I sites to the 3'-end. Primers b and c each bridge both CD8 and DAF sequence, and are complementary to each other at their 5' ends. Hence, the separate CD8 and DAF PCR products, when diluted (1:100), combined, denatured and reannealed, yield a subset of chimeric CD8:DAF molecules, which are then PCR-amplified with the a and d primers (94° C., 2'/37° C., 2'/72° C., 2' for 10 cycles; 94° C., 2'/50° C., 2'/72° C., 2'for the next 20 cycles). The CD8:DAF chimera is gel-purified, digested with Hind III at its ends and ligated into the Hind III site of the Bluescript prokaryotic cloning vector (Stratagene, Inc., San Diego, Calif.). An alternative version of a chimeric CD8:DAF gene, in which the coding sequences for the membrane-proximal O-glycosylation region of DAF are omitted, is produced by substituting primers b and c for primers e[5'-CACTTCCTTTATTTGGCGCTGGCAGGAA-GACC-3'] and f[5'-CAGCGCCAAATAAAG-GAAGTGGAACCACT-3'], respectively. The f and g primer pair PCR amplifies the DAF sequence spanning nucleotide positions 1018 through 2008 (starting at pro 311).

(iii) Production of a soluble CD8 peptide, encompassing the V-homologue domain of CD8 (through ala 114), by a PCR-based site-directed mutagenesis methodology (Ho, S. N., et al. Gene 77:51–59, 1989). Specifically, the CD8 sequence (spanning nucleotide positions 31 through 470) is PCR-amplified with the oligonucleotide primers a (as above) and g[5'-GAGCTC-GAGAAGCTTTTACGCTGGCAGGAAGACCGG-3']. The g primer inserts a stop codon immediately downstream of ala 114 and adds Sac I, Xho I and Hind III sites to the 3' end. The PCR-amplified DNA segment is digested with Hind III and ligated into the Bluescript cloning vector.

(iv) Production of a soluble CD8:MHC conjugate, encompassing the complete extracellular domains of both CD8 and the class I α heavy chain of the A2 haplotype, by a splice-by-overlap-extension methodology. Specifically, primers, with suitable complementary overlap sequences, are used to PCR-amplify and link in-frame the coding sequences for the $\alpha_1$-$\alpha_2$-$\alpha_3$ extracellular multidomain unit of the A2 class I α heavy chain (through trp 274), a linker peptide with minimal secondary structure, and the extracellular domain of CD8 (through asp 161). The linker peptide is comprised of the repeating unit $(Gly.Gly.Gly.Gly.Ser)_3$, and it is generated from complementary oligonucleotides produced on an oligonucleotide synthesizer (PCR-Mate, Applied Biosystems, Inc.). A genetically engineered class I $\beta_2$-microglobulin can be secondarily associated with the class I α chain. Alternatively, an $\alpha_a$-$\alpha_2$ (through thr 182), instead of an $\alpha_1$-$\alpha_2$-$\alpha_3$, MHC multidomain unit is incorporated into such a conjugate. Positioning of the $\alpha_1$-$\alpha_2$ MHC multidomain unit at the amino terminus of either of these linear polypeptide chimeras permits the component $\alpha_1$ and $\alpha_2$ units to fold, as they do in their native state, to constitute an antigen-binding pocket.

(v) Production of a soluble CD8:GM-CSF conjugate, encompassing the complete extracellular region of CD8 (through asp 161) and complete GM-CSF (through glu 127), by a splice-by-overlap-extension methodology. An analogous approach to that used for the CD8:MHC conjugate is used, wherein the coding sequences for GM-CSF, a flexible linker peptide, and CD8's extracellular region are linked. The capacity for binding to GM-CSF receptors is retained by this chimera.

(vi) Production of a soluble CD8:Fcγ1 conjugate, encompassing the complete extracellular domain of human CD8 (through asp 161) and the Fc region of the human IgG1 heavy chain (γ1), by a splice-by-overlap-extension methodology. This CD8:Fc conjugate differs from the CD8:MHC and CD8:GM-CSF conjugates, detailed as examples above, in two ways: 1) this CD8:ligand conjugate has the CD8 component positioned at the amino terminal end of the chimeric protein; and 2) the CD8 and ligand components of this CD8:ligand conjugate are connected to each other without an intervening linker peptide. Primers, with suitable complementary overlap sequences, are used to PCR-amplify and link in-frame the coding sequences for the complete extracellular domain of CD8 and the complete constant region of the human γ1 heavy chain, encompassing the $C_H1.C_H2.C_H3$ multidomain unit starting at ala 114. Specifically, the CD8 sequence (spanning nucleotide positions 31 through 611) is PCR-amplified with the primers a and h [5'-TGGTGGAGCfATCACAGC-GAAGTCCAG-3'], and the γ1 sequence with primers i [5'-CTGTGATGCCTCCACCAACCATCGGT-3'] and j[5'-GTACGTGCCAAGCATCCTCGTGCGACCG-3']. This CD8:Fc conjugate can be isolated by staphylococcus protein A-sepharose chromatography, by virtue of the retained capacity of the Fc domain of the disulfide-linked polypeptide chimera dimer to bind to protein A. In a similar fashion, a soluble CD8:Fcϵ conjugate is assembled, incorporating the $C_H1.C_H2.C_H3.C_H4$ multidomain unit of human IgE. Specifically, the CD8 segment (spanning nucleotide positions 31 through 611; ending at asp 161) is PCR-amplified with primers a and k[5'-GTGTGGATCA-CAGCGAAGTCCAG-3']and ϵ(spanning nucleotide positions 98 through 1847; starting with ala 114) is PCR-amplified with primers l[5'-CTGTGATGCCTC-CACACAGAGCCCATCCGTCTTC-3'] and m[5'-GT-CACAGTGGACAGAAGGTCT-3'].

Branched polypeptide chimeras, in the form of CD8:ligand conjugates, can be readily produced by template-assembled synthetic peptide (TASP) technology (Mutter, M., Trends Biochem. Sci. 13:260–265, 1988). By this process, the peptide units are synthesized separately and covalently coupled to a multifunctional carrier, such as a core peptide, using chemical coupling reagents. For example, a cyclic decapeptide analogue of gramicidin S, in which two antiparallel β-sheet segments (lys-ala-lys) are linked by two β-turns, can be used as a core peptide. Segment condensation strategies can be used to attach CD8 and secondary ligand peptides to the ϵ-amino groups of the 4 lysine side chains. Alternatively, CD8 and ligand components can be covalently linked directly to each other in branched structures using chemical cross-linking reagents. By this methodology, for example, CD8 and Fc dimers can be directly linked. Branched, as opposed to linear, polypeptide chimeras are particularly well-suited for providing for multivalent CD8:ligand conjugates (vide infra), with varying CD8 to ligand ratios.

To facilitate the biochemical isolation of the various CD8 compositions disclosed heretofore, the primary sequence of the CD8 peptide, or in the special case of CD8:ligand conjugates, the primary sequence of either the CD8 or ligand peptides, can be altered through genetic engineering strategies. A particularly useful alteration is the insertion of two or more neighboring histidine residues. This insertion can be in the amino or carboxy terminus of the peptide. Additionally, for CD8:ligand linear polypeptide chimeras, the histidines can also be inserted into the linker peptide, and for CD8:ligand branched polypeptide chimeras, the histidines can also be inserted into the core peptide. Histidine residue insertions can be readily accomplised by the splice-by-overlap extension methodology, by incorporating histidine-encoding CAT and CAC triplet codons into the PCR primers at suitable locations in the coding sequence. Histidine-modified proteins can be efficiently and quantitatively isolated by nickel-sepharose chromatography. The histidine-nickel interaction is based upon protonation, and hence this interaction can be reversed, for purposes of peptide elution, through a simple pH shift. Other primary sequence modifications, such as the insertion of reactive amino acids for specific chemical coupling reagents, can also be performed. Alternatively, more conventional, and considerably less efficient biochemical isolation strategies can be employed, including those based upon immunoaffinity (e.g., anti-CD8 primary antibodies).

Another embodiment of a CD8 composition according to the present invention comprises biomembranes coated with CD8 (and a second ligand) or CD8:ligand peptides. These biomembranes can be in the form of, but are not restricted to, cells, liposomes, planar membranes or pseudocytes (Goldstein, S. A., et al. J. Immunol. 137:3383–3392, 1986). Cells that naturally bear CD8, such as CD8-positive T lymphocytes, or that are coated and/or genetically engineered to bear CD8 can be alternatively utilized. A cellular form that is particularly well-suited, as a therapeutic agent, for modulating cells in the blood compartment are autologous, or heterologous blood group-matched, erythrocytes coated with CD8 peptides. The applicability of liposomes for pharmaceutical purposes has been documented extensively in U.S. patent filings. CD8-coated liposomes, as disclosed in the present invention, can additionally be internally loaded with organic and inorganic constituents, such as cytokines and toxins, to be targeted to specific cells. A glycoinositolphospholipid-modified CD8 peptide is a preferred membrane-binding CD8 composition according to the present invention, to be used for coating biomembranes, since said peptide, so modified, can be readily incorporated into biomembranes in the presence of low, non-lytic concentrations of detergents. Both free cells and cells embedded in a tissue matrix can be coated with glycoinositolphospholipid-modified CD8 peptides. Another coating process entails the use of cross-linking chemical reagents to bind a CD8 peptide to biomembranes. Various processes for covalently coupling peptides to liposomes have been disclosed (see, for example, U.S. Pat. Nos. 4,565,696 and 4,762,915). Yet another means of producing cells coated with a CD8 peptide is through the use of gene transfection technology. By any of these coating processes, multiple additional molecules can be added to the biomembrane to enhance the biological potency of the CD8 peptide. The various acellular therapeutic biomembrane preparations described heretofore can be stored in a dehydrated form, and packaged into kits, for pharmaceutical use.

One embodiment of a CD8-mediated therapeutic process according to the present invention comprises the use of a CD8 peptide, as disclosed in the present invention, to inhibit specific cells in vivo or in vitro. This process is of particular applicability for purposes of specific immunosuppression and immunotolerance induction and derives from our novel finding of CD8's pivotal role in natural immunoregulation. The CD8-mediated inhibitory effect is contingent upon the simultaneous copresentation of a molecular signal that normally, in the absence of CD8, contributes to cellular activation. This second signal can be provided by a second molecule noncovalently associated with CD8, by virtue of its presence on the same biomembrane with CD8, or covalently associated with CD8 in an artificial CD8:ligand conjugate. The nature of the second, noncovalently or covalently, associated ligand dictates the nature of the target cell to be inhibited. Specific T cells can be inhibited by CD8 in association with allogeneic MHC or an MHC:NAP complex. Other specific target cells can be selectively inhibited using other CD8:ligand combinations as cited (vide supra). The treatment of target cells to be inhibited can either be in vitro, prior to infusion of the cell population into the subject, or in vivo, wherein the CD8 composition is administered directly to the subject.

As an example of a CD8-mediated immunomodulatory therapeutic process, the sequence of steps that can be executed for inducing tolerance in a prospective transplant recipient for the allogeneic MHC polypeptides of the transplant donor, in order to prevent imunological rejection of the graft following transplantation, are as follows:

(i) Chimeric gene constructs are assembled, within the Bluescript cloning vector, for producing glycoinositolphospholipid-modified peptide derivatives of human CD8, specific donor allo-class I MHC α heavy chains and specific donor allo-class II MHC α and β chains. In each case, the coding sequence for the extracellular domain of the respective polypeptide is linked in-frame to the 3'-end DAF coding sequence, the latter encompassing the signals that direct the glycoinositolphospholipid modification process inside of cells. In addition, the complete coding sequence for the nonpolymorphic class I MHC $\beta_2$-microglobulin light chain is subcloned into the Bluescript cloning vector. The PCR-based splice-by-overlap-extension methodology is used, as detailed above, to assemble these genetic constructions, and primers designed to insert 4 neighboring histidine residues at the peptide:DAF junction and 3'end of $\beta_2$-microglobulin are employed.

(ii) These coding sequences are mobilized by restriction endonuclease digestion from the Bluescript cloning vector, using flanking restriction endonuclease sites in the multiple cloning site of this vector, and each is inserted into the baculovirus expression vector pVL1392 (obtained from Dr. Max Summers, Texas A&M University) which is suited for gene cassettes containing their own translation initiation signals.

(iii) 2 μg of each expression construct is cotransfected into *Spodoptera frugiperda* (Sf)9 cells in combination with 1 μg *Autographa californica* nuclear polyhedrosis virus DNA, in order to produce recombinant viruses for protein expression. By the fourth day post-transfection, up to 50% of the cells have vital occlusions visible in the nucleus and the virus titer is approximately $10^7$ pfu/ml; recombinant viruses account for up to 5% of the vital plaques. Purification of vital recombinants is achieved by three rounds of plaque purification.

(iv) Each group of Sf9 cells, infected with plaque-purified recombinant virus, is harvested, lysed in 1% NP-40 in phosphate-buffered saline containing 50 g/ml of the synthetic elastase inhibitor Suc(OMe)-Ala-Ala-Pro-Val-MCA (Peninsula Laboratories, Inc., Belmont, Calif.) and 1 mM phenylmethylsulfonylfluoride (Sigma Chemical Co., St. Louis, Mo.). Each detergent lysate is passed over a 5 ml nickel-sepharose column, and in each case, a polypeptide mixture, highly enriched for the respective over-expressed peptide is eluted from the nickel-sepharose matrix by a pH shift, according to the standard protocol, and dialyzed against neutral buffer. Peptides so produced can be prepared in advance and packaged into kits.

(v) Unilamellar liposomes coated with glycoinositolphospholipid-modified CD8, class Iα, class IIα, class IIβ and unmodified class I $\beta_2$-microglobulin are prepared by a detergent dialysis method (see, for example, Milsmann, M., et al. Biochim. Biophys. Acta 512:147, 1978), wherein a mixture is prepared containing egg lecithin, cholesterol, diacetyl phosphate, and glycoinositolphospholipid-modified peptides in a molecular ratio of 2:1.5:0.2:0.01. The mixture is dissolved in a chloroform:methanol solution (2:1) containing 1% sodium cholate, and this lipid-detergent mixture is subsequently rotary evaporated in a round-bottomed flask, depositing a thin dry film. Liposomes form spontaneously when the lipid film is redissolved in phosphate-buffered saline (0.1M, pH 7.3). Detergent and excess reagents are removed by dialysis against several changes of 0.05M Tris, pH 7.8, and the final concentration of these peptide-coated liposomes is adjusted in Tris buffer so that phospholipid content is 12 μmol/L. A broad array of U.S. patent filings describe alternative liposomal compositions, incorporating various synthetic lecithins, modified cholesterols and negative-charged molecules other than diacetyl phosphate, and methods for preparing said liposomal compositions, and these can be readily adapted for preparing CD8-coated liposomes. An alternative to adding the glycoinositolphospholipid-modified peptides to the original mixture of liposomal constituents is to secondarily incorporate said peptides into formed liposomes in the presence of 0.003% NP-40. These peptide-coated liposomes can be stored in a dehydrated state and packaged into kits (see, for example, U.S. Pat. Nos. 4,746,516 and 4,766,046) or used immediately for immunomodulation.

(vi) A subject who is to undergo a transplant is assessed for alloreactivity to donor allo-MHC by isolating peripheral blood mononuclear cells from the prospective transplant recipient's blood, and setting up a mixed lymphocyte reaction (MLR) with these recipient PBMC as responders and irradiated (5000 R) donor PBMC as stimulators. If a significant proliferative response is noted, a pharmaceutical composition comprising the peptide-coated liposomes, corresponding to donor allo-MHC, are infused intravenously 6–8 weeks prior to the planned transplantation procedure;

(vii) At 3–4 weeks prior to the transplantation date, the in vitro MLR assay is repeated, and if a residual proliferative response between recipient responders and donor stimulators persists, the coated liposome preparation is reinfused;

(viii) To further enhance engraftment, cells of the graft are coated with CD8 prior to transplantation (vide infra).

(ix) The MLR assay is repeated at 6 month intervals post-transplantation, and booster doses of the CD8 composition are administered systemically as required.

Of note with respect to this particular example of an immunomodulatory process for prospective transplant recipients are the following: 1) Polymerase chain reaction technology now permits the expeditious cloning of the array of allo-MHCs that are present in the human population, and this technology further provides for the rapid assembly of MHC.DAF gene chimeras. 2) Nominal antigen peptides (NAPs), representing processed peptides of MHC and other polypeptides, can be added to liposomes or other therapeutic biomembrane preparations bearing CD8 and self-MHC, for immunomodulation to both allogeneic and other antigens. This approach permits the treatment of the broad range of autoimmune, allergic and other human diseases where there are unwanted, specific T cell immunoreactivities. 3) Instead of using liposomes (or other therapeutic biomembrane preparations) coated with separate CD8 and allo-MHC peptides, liposomes coated with CD8:MHC (covalent) conjugates or soluble CD8:MHC (covalent) conjugates can be administered to the prospective transplant recipient.

The effective subunit valency of the CD8 and ligand components in soluble CD8:ligand conjugates dictates the potency of the biological effect exerted upon target cells. Multivalent conjugates, wherein more than one CD8 peptide subunit and/or more than one ligand subunit are covalently linked in each conjugate molecule, are functional equivalents of membrane-linked multimolecular CD8:ligand combinations. In contrast, univalent conjugates, wherein one CD8 peptide subunit and one ligand subunit are covalently linked in each conjugate molecule, can, in certain instances, demonstrate lower efficacy. In vitro cellular assays, such as mixed lymphocyte cultures and colony forming assays, that can be used to predict the in vivo effect of a given CD8:ligand conjugate, with a defined subunit valency, are well known to those familiar with the art. Furthermore, in vivo assessment of the activity of a given CD8 composition can be performed in a suitable experimental animal. For instance, human CD8 compositions can be studied in severe combined immunodeficiency disease (SCID) mice reconstituted with human immune systems.

Another embodiment of a CD8-mediated therapeutic process according to the present invention comprises the use of CD8:Fc conjugates for generalized, nonspecific immunosuppression. These conjugates, in their soluble forms, bind to Fc receptors (FcR) on various FcR-bearing cells in an immunoglobulin isotype-specific fashion. Antigen presenting cells, one set of cells that bear FcRs on their surfaces, can in this way be coated with CD8, and in turn, the antigen-specific activation function of these cells can thereby be converted to an antigen-specific inhibition function. This, in effect, provides a way to block all antigen presenting cell-dependent immune responses in a general fashion.

Another therapeutic application for CD8:Fc conjugates is the inhibition of specific FcR-bearing cells. This is of particular relevance for the therapy of allergic disorders, such as atopic (IgE-mediated) asthma, where Fcϵ-mediated degranulation of FceR-positive mast cells and basophils, leading to the release of mediators such as histamine, is a primary pathogenetic mechanism. A CD8:Fcϵ conjugate can be used to eliminate the untoward functional reactivities of these FcϵR-positive cells. The Fcsϵ sequence can be derived from either soluble of membrane ϵ heavy chain, and differences in the carboxy termini of these Fcϵ derivatives can influence regulatory T cell-based molecular interactions. For example, a CD8-Fcϵ conjugate, or a therapeutic biomembrane preparation bearing CD8 and Fcϵ peptide units, is administered parenterally to an allergic subject at 6 month intevals. Allergy testing is performed yearly to monitor the therapeutic response. For subjects with upper airway manifestations of their allergic disease, intranasal and inhalant drug formulations are particularly efficacious.

The use of CD8:Fcϵ conjugates for inactivating FcϵR-bearing cells in allergic subjects represents a specialized application of the more general principle that CD8-mediated inhibition can be applied in a pharmaceutical context for inhibiting a broad array of cell types. For example, a CD8: monocyte/macrophage-colony stimulating factor (M-CSF) conjugate can be used to inhibit M-CSFR-bearing cells that can normally be activated by M-CSF. This provides a therapeutic approach for dealing with clinical conditions in which there is excessive production of normal or transformed monocytes. Similarly, CD8:GM-CSF can be used to inhibit granulocyte-macrophage precursors. The nature of the target cells and the potential clinical applications for the various CD8:ligand conjugates disclosed in the present invention will be apparent to those familiar with the art.

Yet another embodiment of a CD8-mediated therapeutic process according to the present invention comprises the use of CD8 peptides to promote engraftment of cells, tissues and organs, such as kidney, heart, skin, and bone marrow. According to a preferred embodiment of this process, cells of a graft are coated with a membrane-binding CD8 peptide, and the graft, comprising CD8-coated cells, is then transplanted into the recipient. Glycoinositolphospholipid-modified CD8 peptides are membrane-binding CD8 compositions well-suited for this purpose, since, peptides so modified spontaneously incorporate into cellular membranes in the presence of low, non-lytic concentrations of detergents (e.g., 0.003% NP-40; J. Exp. Med. 160:1558–1578, 1984). Coexpression of CD8 and allo-MHC on the graft cells serves to inhibit alloreactive T cells, and thereby prolong graft survival through suppression of the rejection process. This process is applicable to a broad array of graft types. In the case of a vascularized solid tissue graft, the organ can be perfused with a membrane-binding CD8 composition in order to coat the endothelial cells of the graft. Exogenously introduced CD8, in association with endogenously expressed allo-MHC, on graft endothelial cells serves to inhibit allospecific host immune cells entering the tissue or organ and to mitigate acute graft rejection processes directed against the endothelial lining. In the case of bone marrow and other grafts comprised of dispersed cells, CD8-coating of the cells to be engrafted can be accomplished by combining the cells and a membrane-binding CD8 composition together as a suspension in a tissue culture flask. Not only are the CD8-coated cells themselves protected from immunological rejection, but the transplantation of such CD8-coated graft cells into a given body compartment further serves to convert said compartment into an immunologically privileged site for all cells with a shared allogeneic phenotype. This is of particular utility when long-lived graft cells are used. For example, allogeneic human bone marrow stromal cells can be coated with CD8 in vitro and transplanted into the host to convert the host's bone marrow into an immunologically privileged site for other cells with a shared allogeneic phenotype that can be engrafted at later times.

The clinical setting of renal transplantation serves to exemplify a CD8-coating process for pretreating a solid organ graft prior to transplantation, in order to block immunological rejection of the graft following transplantation, and the sequence of steps that can be executed in this case are:

(i) The kidney of a renal transplant donor is perfused, at the time of surgery and prior to its resection, with 1 ml of a solution containing a glycoinositolphospholipid-modified CD8 peptide composition (vide supra) via a bolus injection into the renal artery supplying that kidney, or alternatively, via a bolus infusion into said renal artery by means of renal arterial catheterization prior to surgery. The infused solution comprises the membrane-binding CD8 peptide in a 0.003% NP-40-containing normal saline diluent.

(ii) The kidney, once resected, is kept at 4° C. in a perfusate supplemented with the membrane-binding CD8 peptide in 0.003% NP-40 until transplantation into the recipient.

The clinical setting of bone marrow transplantation serves to exemplify a CD8-coating process for pretreating graft cells that are in a dispersed state prior to transplantation, in order to block immunological rejection of the graft cells following transplantation, and the sequence of steps that can be executed in this case are:

(i) Bone marrow (approximately 15 cc/kg body weight for an adult) is aspirated from a donor by methods well known in the art (see, for example, U.S. Pat. Nos. 4,481,946 and 4,486,188), and is immediately placed into cold TC-199 medium (Gibco, Inc.) supplemented with heparin (30,000 U/100 ml).

(ii) The bone marrow suspension is centrifuged in a Sorvall RC-3 at 3000 rpm, 20', at ambient temperature. The plasma supernatant is separated, and stored for later use. The marrow is transferred to 15 ml sterile polypropylene tubes, and these are centrifuged at 1500 g, 10', at 4° C.

(iii) The marrow buffy coat is recovered and transferred into a 2000 ml transfer pack for peptide-coating. The nucleated marrow cells are adjusted to a final concentration of $2\times10^7$ cells/ml, and hematocrit to <10% with TC-199 medium.

(iv) NP-40 is added to the bone marrow suspension to a final concentration of 0.003%, and a glycoinositolphospholipid-modified CD8 peptide composition in 0.003% NP-40 is added immediately thereafter. The mixture is incubated for 30' at ambient temperature, and the transfer pack is gently agitated every 5'.

(v) The bone marrow cells are transferred into cold satellite bags, and washed free of detergent and unbound CD8 peptide by serial centrifugation (RC-3, 2200 g, 4° C., 10'each spin). The marrow cells are diluted with cold, irradiated autologous plasma to $8\times10^7$ nucleated cells/ml.

(vi) A 2 ml sample is taken for in vitro assays, and processed by diluting 1:3 with cold TC-199, layering over 3 ml Ficoll-Hypaque (Pharmacia, Inc.), and centrifuging (500 g, 30', ambient temperature). The mononuclear cell layer is thrice washed and assessed for colony formation capacity in methyl cellulose.

(vii) The remaining CD8-coated cells are mixed with cold freezing solution [60 ml TC-199+20 ml DMSO (Cryoserv Research Industries Corp.) +20 ml irradiated, autologous plasma] at a 1:1 cell ratio.The cells are then incrementally frozen using computerized cryotechnological equipment (e.g., U.S. Pat Nos. 4,107,937 and 4,117,881) and stored in liquid nitrogen until infusion into the recipient.

The CD8 coating process is applicable to isografts, homografts, heterografts and xenografts. CD8-coated cells, tissues and organs provide for "universal" donor material, permitting the circumvention of the limiting requirement imposed by currently available transplantation technologies for histocompatible cells, tissues and organs. For example, CD8-coated epidermal cells can be used in a universal way for skin transplantation. The CD8 coating process can be applied not only to native, unmodified cells, but also to genetically engineered, or otherwise engineered, cells. This permits the sustained delivery of a defined gene product, to a subject in need of said product, by using a CD8-coated cell as a cellular vehicle that can evade the host's immunological rejection mechanisms. For example, a transcriptional cassette, comprising the insulin gene driven by a suitable regulatory promoter element, can be transfected into human bone marrow stromal cells, and these engineered cells can be coated with CD8 and transplanted into a diabetic subject, in order to correct such a subject's insulin deficiency. In the particular case of xenografts, the CD8 coating process offers the possibility of generating animal chimeras for experimental purposes. For example, a mouse can be reconstituted with murine CD8-coated human hematopoietic progenitor cells. This bypasses the limitation of methodologies currently employed for generating mouse-human chimeras, such as the reconstitution of a SCID mouse with human hematopoietic progenitor cells, which require the use of an immunodeficient, and consequently hard to maintain, mouse as a host for the human cells.

As described above, in addition to coating the graft cells with CD8, engraftment can be enhanced by pretreating the graft recipient with therapeutic biomembrane preparations bearing CD8 and allo-MHC or with soluble CD8:MHC conjugates prior to transplantation, in order to induce specific immunotolerance to the allo-MHC of the transplanted cells, tissues or organs. Biomembrane compositions that can be used for this purpose comprise native or engineered cells, liposomes, planar membranes, or pseudocytes. CD8:MHC conjugates comprising both class I and class II MHC components can be coadministered.

Still another embodiment of a CD8-mediated therapeutic process according to the present invention comprises the use of CD8 peptides to prevent graft versus-host disease when bone marrow is transplanted to a non-identical recipient. A therapeutic biomembrane preparation, bearing both CD8 and host MHC peptides or a CD8:MHC conjugate is added to donor bone marrow cells in vitro, and following variable incubation periods, the cells are infused into the transplant recipient. This form of treatment eliminates alloreactive immune cells amidst the donor bone marrow cells, and mitigates the requirement for T-cell depleting the bone marrow.

In the clinical situation of bone marrow transplantation, the various CD8-dependent inhibitory processes described heretofore can be combined in a multifacted way to inhibit both host-versus-graft and graft-versus-host responses. As an example, a sequence of steps that can be executed in this setting are:

(i) A CD8 peptide composition, comprising CD8 and donor allo-MHC, is administered to the transplant recipient 6–8 weeks prior to transplantation, with a booster dose at 3–4 weeks, if required, in order to suppress alloreactive cells of the recipient.

(ii) Bone marrow is aspirated from the donor, NP-40 is added to the suspension to a final concentration of 0.003%, and a CD8 peptide composition, comprising CD8 and recipient allo-MHC, is added to the bone marrow cells, incubated for 4 h at 37° C., in order to inhibit alloreactive cells of bone marrow cell population.

(iii) Bone marrow cells are coated with a CD8 peptide composition, comprising a membrane-binding CD8 peptide, and the cells are either stored in cryopreservative in liquid nitrogen until use or immediately infused into the transplant recipient.

The compositions active in the novel methods of treatment of this invention can be administered in a wide variety of therapeutic dosage forms in conventional vehicles. A variety of effective formulations for peptide pharmaceuticals, as well as dosing schedules for immunomodulatory agents, are known to those familiar with the art and can be applied to the CD8 peptides disclosed heretofore. Non-immunogenic carriers, such as carboxymethyl cellulose (U.S. Pat. No. 4,415,552), are particularly well suited for soluble CD8 compositions. Therapeutic cellular preparations for CD8-based therapy are infused intravenously into the subject. Therapeutic liposome and other planar membrane preparations for CD8-based therapy can be administered parenterally or orally. Modulation of target cells is accomplished by administering to a subject, or treating cells of a subject in vitro, with a dose, or series of doses which will achieve the desired modulatory effect. The efficacy of cellular modulation, such as the degree of CD8-mediated immunosuppression, can be easily monitored using conventional in vivo and in vitro immunological testing methods, and booster doses can be administered as needed.

It is understood that various other modifications will be apparent to and can readily be made by those skilled in the art without departing from the scope and spirit of this invention. Accordingly, it is not intended that the scope of the claims appended hereto be limited to the description as set forth above, but rather that the claims be construed as encompassing all the features of patentable novelty, ensuing from the disclosure of CD8's inhibitory ligand activity, which would be treated as equivalents thereof by those skilled in the art to which this invention pertains.

We claim:

1. A CD8 polypeptide conjugate useful for producing an artificial veto cell, comprising:

an extracellular domain portion of CD8 comprising amino acid positions 1–114 which is able to bind a T cell isolated from a human responder peripheral blood mononuclear cell population and reduce the rate of proliferation of said T cell; and covalently linked to said portion of CD8, a molecule adapted to bind covalently or non-covalently with a antigen presenting cell surface molecule, said molecule not naturally being covalently linked to said extracellular domain portion of said CD8;

wherein said extracellular domain portion and said molecule are linked in a manner which allows said extracellular domain portion to bind said T cell and reduce the rate of proliferation of said T cell, and allows said molecule to bind said antigen presenting cell surface molecule.

2. A CD8 polypeptide conjugate useful for producing an artificial veto cell, comprising:

an extracellular domain portion of CD8 comprising amino acid positions 1–114 which is able to bind an a T cell isolated from a human responder peripheral blood mononuclear cell population and reduce the rate of proliferation of said T cell, and covalently linked to said portion of CD8, a molecule comprising a membrane binding portion not naturally covalently linked to said extracellular domain of CD8;

wherein said molecule is adapted to incorporate into a lipid membrane and non-covalently or covalently associate with said lipid membrane, and said extracellular domain portion and said molecule are linked in a manner which allows said extracellular domain portion to bind said T cell and reduce the rate of proliferation of said T cell, and allows said molecule to incorporate into said lipid membrane.

3. The CD8 polypeptide conjugate of claim 1, or 2, wherein said extracellular domain portion of CD8 consists of amino acids 1–114 of human CD8.

4. The CD8 polypeptide conjugate of claim 1 or 2, wherein said extracellular domain portion comprises at least two histidine residues.

5. The CD8 polypeptide conjugate of claim 1, wherein said molecule comprises an immunoglobulin Fc domain.

6. The CD8 polypeptide conjugate of claim 5, wherein said Fc domain is that domain present in immunoglobulin IgGl or IgE.

7. The CD8 polypeptide conjugate of claim 1, wherein said molecule comprises an IgFv domain.

8. The CD8 polypeptide conjugate of claim 1, wherein said molecule comprises a cytokine.

9. The CD8 polypeptide conjugate of claim 1, wherein said molecule comprises a lectin.

10. The CD8 polypeptide conjugate of claim 1, wherein said molecule comprises an antiidiotypic antibody.

11. The CD8 polypeptide conjugate of claims 1 or 2 wherein said molecule comprises a glycoinosotolphospholipid.

12. A lipid membrane comprising a CD8 polypeptide conjugate of claim 1 or 2.

13. The lipid membrane of claim 12, wherein said membrane forms part of a cell or a liposome.

14. A therapeutic composition comprising a therapeutically effective amount of a CD8 polypeptide conjugate of claims 1 or 2 admixed in a pharmaceutically acceptable buffer.

15. An antigen presenting cell comprising a CD8 conjugate of either claim 1 or claim 2, wherein said antigen presenting cell presents in, or on its surface the extracellular domain portion of CD8.

16. The antigen presenting cell of claim 15 wherein the extracellular domain portion of CD8 consists of amino acid residues 1–114 of human CD8.

17. The antigen presenting cell of claim 15, wherein said extracellular domain portion of CD8 comprises amino acids 1–161 of human CD8.

18. The antigen presenting cell of claim 15, wherein said extracellular domain portion comprises at least two histidine residues.

19. The antigen presenting cell of claim 15, wherein said extracellular domain portion comprises the immunoglobulin-like domain of CD8.

20. A method for introducing a CD8 polypeptide conjugate into a membrane, comprising contacting a CD8 polypeptide conjugate of either claim 1 or claim 2 with a cell membrane under conditions sufficient for membrane binding or incorporation to occur.

21. The method of claim 20, wherein said extracellular domain portion of CD8 consists of amino acids 1–114 of human CD8.

22. The method of claim 20, wherein said extracellular domain portion of CD8 comprises amino acids 1–161 of human CD8.

23. The method of claim 20 wherein said extracellular domain portion comprises at least two histidine residues.

24. The method of claim 20, wherein said extracellular domain portion comprises the immunoglobulin-like domain of CD8.

25. The method of claim 20, wherein said molecule comprises a glycoinosotolphospholipid.

* * * * *

UNITED STATES PATENT AND TRADEMARK OFFICE

CERTIFICATE OF CORRECTION

PATENT NO. : 5,623,056

DATED : April 22, 1997

INVENTOR(S) : Mark L. Tykocinski and David R. Kaplan

It is certified that error appears in the above-indentified patent and that said Letters Patent is hereby corrected as shown below:

On the title page in the left column in the title after CD replace "S" with --8--

Column 1, line 1: after CD replace "S" with --8--

Signed and Sealed this

Ninth Day of September, 1997

Attest:

BRUCE LEHMAN

*Attesting Officer*

*Commissioner of Patents and Trademarks*